United States Patent [19]

Atkinson

[11] Patent Number: 4,794,800

[45] Date of Patent: Jan. 3, 1989

[54] WIRE SENSING AND MEASUREMENT APPARATUS

[75] Inventor: Bobby Atkinson, Fontana, Calif.

[73] Assignee: General Dynamics Corporation, Pomona, Calif.

[21] Appl. No.: 103,461

[22] Filed: Oct. 1, 1987

[51] Int. Cl.$^4$ .............................................. G01N 3/08
[52] U.S. Cl. .............................................. 73/827
[58] Field of Search ................ 73/827, 834, 828, 830; 356/429, 72, 73, 384, 385, 386, 387; 250/560, 571; 364/563; 228/104; 372/24, 19, 17

[56] References Cited

U.S. PATENT DOCUMENTS

| | | | |
|---|---|---|---|
| 3,564,911 | 2/1971 | Slemmons et al. | 73/827 X |
| 3,572,108 | 3/1971 | McShane et al. | 73/827 |
| 3,712,741 | 1/1973 | Revert | 356/387 |
| 3,856,412 | 12/1974 | Zanoni | 356/386 |
| 3,906,238 | 9/1975 | Yagi et al. | 356/387 |
| 3,910,105 | 10/1975 | Hoffstedt | 73/800 |
| 4,131,365 | 12/1978 | Pryor | 356/387 |
| 4,194,392 | 3/1980 | Lombard et al. | 73/827 X |
| 4,198,165 | 4/1980 | Kirschstein | 356/386 |
| 4,213,556 | 7/1980 | Persson et al. | 73/827 X |
| 4,269,506 | 5/1981 | Johnson et al. | 73/800 X |
| 4,405,231 | 9/1983 | Shemyakin et al. | 73/800 X |
| 4,453,414 | 6/1984 | Ronemus et al. | 73/827 |
| 4,475,812 | 10/1984 | Buczek et al. | 73/800 X |
| 4,492,473 | 1/1985 | Richter et al. | 356/387 |
| 4,495,819 | 1/1985 | Tekippe | 73/800 X |
| 4,502,823 | 3/1985 | Wronski et al. | 250/561 |
| 4,577,100 | 3/1986 | Meltz et al. | 73/800 X |
| 4,603,252 | 7/1986 | Malek et al. | 73/800 X |

FOREIGN PATENT DOCUMENTS 2057120  3/1981  United Kingdom .

OTHER PUBLICATIONS

Taylor, "Using a Laser Micrometer For Precision Control of Wire Diameter and Position On a CV Line", Conference: 13th, 23rd International Wire and Cable Symposium, Atlantic City, NJ (Dec. 1974).

Primary Examiner—Stewart J. Levy
Assistant Examiner—Robert R. Raevis
Attorney, Agent, or Firm—Neil F. Martin; Angus C. Fox

[57] ABSTRACT

A wire sensing and measurement apparatus comprises an optical fiber having a hook shape formed at one end and connected to an optical pulse generator at the opposite end for transmitting a continuous stream of optical pulses to the free end of the hook. An optical detector is positioned opposite the free end of the hook to detect pulses emitted from the hook, and is connected to a missing pulse monitor for monitoring the output of the detector to detect any missing pulses in the sequence. The monitor produces an output pulse for each missing pulse detected. The hook is moved beneath expected wire positions and any wire passing between the free end of the hook and the detector will interrupt the stream of pulses, allowing the wire position to be located. The fiber optic hook may be used as part of a wire pull test machine for testing the strength of electrical circuit wires.

6 Claims, 2 Drawing Sheets

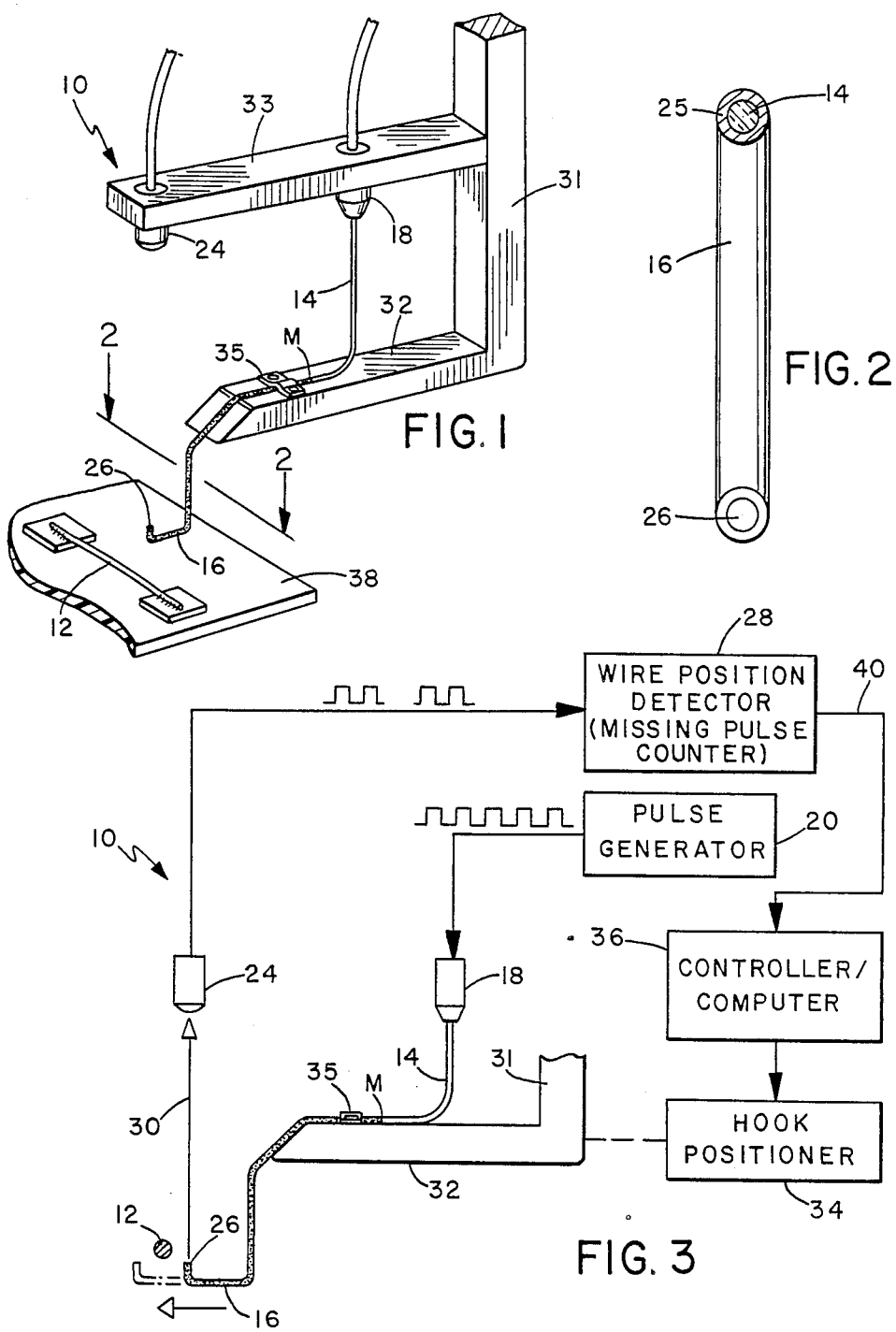

WIRE SENSING AND MEASUREMENT APPARATUS

BACKGROUND OF THE INVENTION

The present invention relates generally to a wire sensing and measurement apparatus, and more particularly to such an apparatus for use in a wire pull machine for pull testing of electrical circuit wires.

Wire pull testing machines are used to determine the bond strength of leads which are attached to circuits. Machines of this type are described, for example, in U.S. Pat. Nos. 4,453,414 of Ronemus et al., 3,564,911 of Slemmons et al., and 3,572,108 of McShane et al. Generally, these machines comprise a wire hook member for hooking under a lead which is then moved away from the lead to apply a pulling force to the lead to test its strength. In some machines of this type a predetermined force is applied to the lead to test whether or not it will break or separate from the circuit under such loads. In other machines the wire is destructively tested by pulling until the wire or bond fails, and the force required is measured and used to adjust the wire bonding equipment, if necessary.

One problem with these wire pull testing machines is that they are commonly positioned by eye. This can be a problem in very small scale, microelectronic circuits involving many wire leads, since there is a good chance that the operator may miss one or more of the leads. Some automatic wire pull machines have been proposed which are programmed with all the wire positions and automatically position the pull hook beneath each stored wire position. However, these machines are also not sufficiently accurate since the position of all the wires in the circuit need not necessarily correspond precisely with the expected, stored wire position, for example if they have been displaced for some reason. In this case the machine will miss some of the wires altogether, as it is only capable of moving the hook sequentially to the stored wire positions. This results in an incomplete, and therefore unsatisfactory, test.

SUMMARY OF THE INVENTION

It is an object of the present invention to provide an apparatus for detecting and measuring wires, which is particularly suitable for use in a wire pull testing machine.

According to the present invention a wire detecting and measurement apparatus is provided, which comprises an optical fiber formed into a hook at one end, a pulse generating device connected to the opposite end of the fiber for transmitting a continuous stream of optical pulses along the fiber, and a pulse detector situated opposite the hooked end of the fiber for detecting optical pulses transmitted from the free end of the fiber. The detector is connected to a missing pulse counter for detecting any missing pulses in the stream of pulses detected from the hooked end of the fiber. The presence of one or more missing pulses indicates the presence of an object, such as a wire, in the path of pulses emitted from the free, hooked end of the fiber.

The free, hooked end of the fiber is polished to form a lens for emitting light pulses from the free end of the hook.

Preferably the hooked end of the fiber is moved beneath expected wire positions automatically and its position adjusted until a missing pulse is detected. This indicates the precise wire position. The hooked end is moved beneath the wire at a fixed speed so that the number of missing pulses provides an indication of the wire diameter. The missing pulse detector preferably includes a counter for counting the number of missing pulses to provide an indication of wire diameter.

The wire detecting and measurement apparatus preferably comprises part of an automatic wire pull testing machine, including a computer for storing information on the expected position of each wire in a circuit, and a hook drive or positioner controlled by the computer and linked to the optical fiber for moving the hook to each expected wire position successively. The computer controls the hook positioner to move the hook to the vicinity of an expected wire position, and then to scan with the hook transversely in a linear path across the expected wire position, monitoring the output of the missing pulse detector during the scan. As soon as a missing pulse is detected, the computer will position the hook for the wire pull test, calculate the wire diameter from the number of missing pulses counted, and set the wire pull loading according to the wire diameter. The wire is then pulled. After the pull test, the hook will be moved to the vicinity of the next stored wire position and the procedure will be repeated. An automatic wire pull testing machine incorporating the wire detection apparatus of this invention can scan and test miniature circuits having 700 or more connecting wires quickly and more reliably than previous automatic wire testing machines. The wire detection apparatus may also be included in manual wire pull testing machines to allow the operator to detect wire positions while moving the hook manually.

The wire detection and measurement apparatus of this invention is not limited to use in wire pull testing machines but may be used in any application where precise wire location information is desired. It allows a wire to be located and measured without requiring any form of physical contact with the wire.

BRIEF DESCRIPTION OF THE DRAWINGS

The present invention will be better understood from the following detailed description of a preferred embodiment, taken in conjunction with the accompanying drawings in which like reference numerals refer to like parts and in which:

FIG. 1 is a perspective view of part of a wire detection and measurement apparatus according to a preferred embodiment of the present invention;

FIG. 2 is an enlarged sectional view of the hook of FIG. 1, taken on the lines 2—2 of FIG. 1;

FIG. 3 is a schematic arrangement showing the connection of the hook in a control apparatus forming part of a wire pull testing machine.

DESCRIPTION OF THE PREFERRED EMBODIMENT

Figure 4:
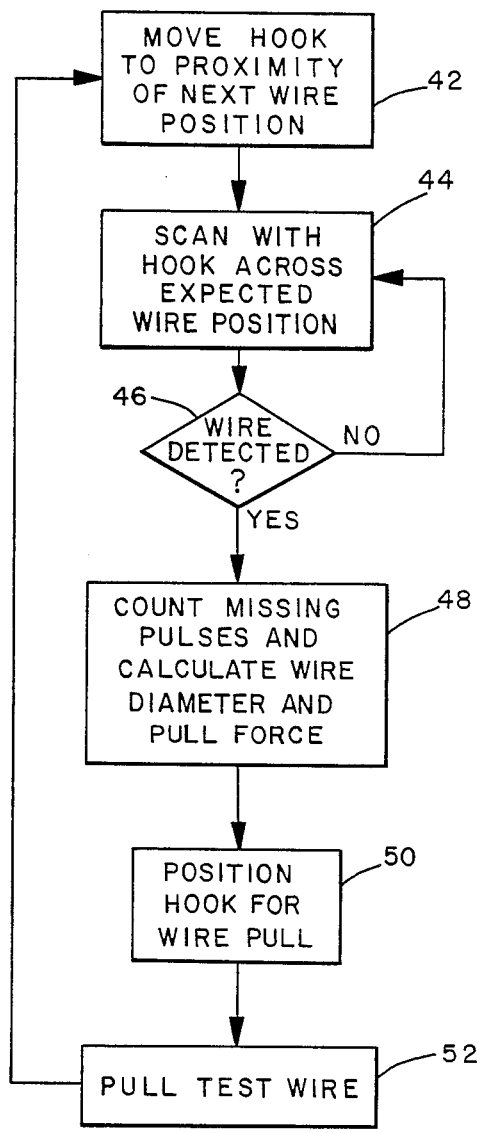
FIG. 4 is a block function diagram of the wire test apparatus.

FIGS. 1 to 3 illustrate a wire detection and measurement apparatus 10 according to a preferred embodiment of the present invention. In the embodiment illustrated, apparatus 10 forms part of a wire pull testing machine for testing the bond strength of circuit connecting wires 12, one of which is shown schematically in FIGS. 1 and 3. The wire pull testing machine may be of a standard type, apart from the modifications described below to incorporate the apparatus 10. The wire detection and measurement apparatus of this invention is not limited to use in wire pull testing machines but may be used in other applications where the locations and dimensions of wires are required.

The apparatus 10 basically comprises an optical fiber 14 which is shaped to form a hook 16 at one end. The opposite end of the fiber 14 is connected to an infrared laser diode source 18, which is connected to the output of an electrical pulse generating circuit 20. Electrical pulses from circuit 20 generate corresponding optical pulses from the laser diode 18 which are transmitted along fiber 14. An infrared light detector 24 is suitably mounted above the free end 26 of hook 16 to detect pulses emitted from the hook. The detector converts the incoming stream of light pulses into electrical pulses at its output, which is connected to a suitable missing pulse monitor and counter circuit 28. The circuit 28 is a timer circuit which times the interval between pulses. If a pulse arrives within a predetermined time interval corresponding to the interval between pulses transmitted from the infrared laser diode, the circuit is reset and the timer restarts. If no pulse arrives within the predetermined time interval, the circuit itself begins to generate pulses, until the next pulse is received from the detector. The pulses generated are counted by a suitable counter, which may be part of the monitor circuit, to produce an output proportional to the diameter of a wire interrupting the pulsed output from the end of the hook. Alternatively, the pulse output of monitor circuit 28 may be input to a computer which counts the number of pulses and uses that result to calculate the wire diameter, in a manner which will be understood by those skilled in the field.

The hook shaped end 16 of fiber 14 is formed by heating and then bending the fiber. In the preferred embodiment of the invention, a thin layer of vacuum deposited metal is then applied to the hook shaped area of the fiber. A thick plating or layer 25 of metal is then applied to the hook to impart greater strength to the hook shaped area. The metal coating preferably extends along the fiber from end 26 to a point about halfway along the fiber, as indicated in FIG. 1. The free end 26 of the hook is polished to form a lens for emitting light pulses 30 from end 26.

As indicated in FIG. 1, the fiber is mounted on an arm 32 projecting from support 31 of a conventional wire pull machine, which may be of the manual or automatic type. The fiber may be secured by a suitable securing device such as bolt 35. A support member 33 extends above the arm as shown in FIG. 1 for supporting the infrared laser coupled to one end of the optical fiber and also supporting the infrared detector at a position directly above the free end of hook 16.

In the preferred embodiment of the invention the wire pull machine is of the automatic type which includes a suitable drive 34 for the arm and a controller or computer 36 for automatically operating the drive 34 to move the hook to a series of stored wire positions on a circuit 38. The machine may be operated either to pull test wires to a predetermined loading and then release, or may be operated in a destructive mode to pull test wires until they break or separate from the circuit. This latter mode is generally used in initial set-up of a wire bonder for adjusting the bonder setting to produce a desired bond strength.

FIG. 3 is a schematic block diagram illustrating the control circuit for controlling movement of the arm 32, and thus the hook. In the present invention this circuit is modified to include a connection 40 to the missing pulse monitor for providing the controller 36 with precise wire position information. FIG. 4 is a flow diagram of the computer program for controlling movement of the hook and application of pull force to the hook.

The operation of the apparatus shown in FIG. 3 is as follows. The computer 36 is programmed to move the arm successively into the vicinity of each of a series of stored expected wire positions on a circuit (step 42 in FIG. 4). The hooked end is scanned in a linear path transversely across the expected wire position from a position to one side of the expected position and across the expected position to the opposite side (step 44). During the scan, the computer monitors the output of the missing pulse detector circuit (step 46). As soon as the wire is positioned between the free end of the hook 16 and the infrared detector, it interrupts the pulsed output from the hooked end of the fiber, and this interruption will be detected by the missing pulse monitor. The missing pulse monitor will produce one output pulse in response to each missing pulse detected, and thus the number of output pulses produced by the monitor circuit will be proportional to the wire diameter. The transverse speed of the hook together with the number of missing pulses detected indicates the actual diameter of the wire.

Once the wire has been located and the number of missing pulses counted (step 48), no further scanning is required and the controller operates the drive to position the hook below the wire (step 50). The positioner then pulls up the arm, and thus the hook, pulling up the retained wire and testing its strength. The machine may either be of the type which applies a predetermined pulling force to the wire to test if it is strong enough to withstand that force, or of the destructive type which pulls the wire until it breaks or the bond fails, to provide data on desirable bond strengths to be used in a wire bonding machine. Most wire pull testing machines can be used in either the destructive or non-destructive mode. In the non-destructive case, the wire diameter information may be used to adjust the pulling force applied to the wire, so that a larger pulling force is applied to thicker wires (step 50), before the actual wire pulling step 52 is carried out.

Thus the vicinity of each expected wire position will be scanned until an output pulse is received from the missing pulse monitor. The hook can then be accurately positioned beneath the wire and an upward force can be applied to pull test the wire. This substantially reduces the risk of wires being missed and the test being incomplete.

The computer then controls the hook drive to move the fiber to the vicinity of the next expected wire position, and repeats the scanning process to locate the precise position of the wire. With this technique, there is considerably less risk of missing some of the wires on a circuit, since the position of each expected wire can be located, even if the wire is not in the exact position expected. The wire pull machine can be made fully automatic so that very small scale, miniature circuits involving up to 700 or more connecting wires can be pull tested quickly and relatively accurately.

The fiber optic hook is coated with metal as described above to impart sufficient strength to the hook to enable it to pull test straight wires. The wire detection and measurement apparatus of this invention may be used alone or in conjunction with a wire pull test machine as described above. In each case the apparatus enables wires to be located and their diameter measured without requiring any form of physical contact with the wires. In the case of automatic wire pull testing machines, this apparatus substantially reduces the risk of incomplete testing as the result of misplaced wires. The detected wire diameter information allows the pull force to be adjusted for thicker or thinner wires.

Although a preferred embodiment of the present invention has been described above by way of example only, it will be understood by those skilled in the field that modifications may be made to the disclosed embodiment without departing from the scope of the invention, which is defined by the appended claims.

I claim:

1. A wire pull test machine for testing the bond strength of connecting wires in an electrical circuit, comprising:
   an optical fiber formed into a hook at one end;
   an optical pulse generator coupled to the opposite end of the fiber for transmitting a continuous stream of pulses through the fiber;
   an optical detector positioned opposite the hooked end of the fiber for detecting optical pulses emitted from said hooked end;
   a missing pulse monitor connected to the optical detector for detecting any missing pulses in the pulse stream detected by the detector and for producing an output control pulse in response to each missing pulse detected;
   drive means linked to the optical fiber for moving the hooked end of the fiber beneath a wire positioned on the electrical circuit and for pulling on a wire held in the hooked end; and
   control means linked to the missing pulse monitor and to the drive means for controlling movement of the fiber comprising means for scanning with the hooked end of the fiber to detect the position of each wire on the electrical circuit in response to a control pulse from the missing pulse monitor, and for applying a pulling force to a wire located in the hook in response to detection of a wire.

2. The machine as claimed in claim 1, wherein the hook-shaped end is coated with metal.

3. The machine as claimed in claim 1, in which the free end of the fiber is formed into a lens.

4. The machine as claimed in claim 1, including counter means connected to the missing pulse monitor for counting the output pulses and producing an output proportional to the wire diameter.

5. The machine as claimed in claim 1, wherein the pulse generator comprises an infrared laser diode and an electrical pulse generator connected to the laser diode.

6. A method of testing the bond strength of connecting wires in an electrical circuit, comprising the steps of:
   supplying a continuous stream of optical pulses to one end of an optical fiber having its opposite end formed into a hook;
   moving the optical fiber so that its hooked end passes transversely beneath an expected wire position on the electrical circuit;
   detecting output pulses emitted from the hooked end of the fiber and monitoring the pulses to detect any missing pulses in the sequence as the result of a wire passing between the hooked end of the fiber and the detector;
   using the missing pulse information to control positioning of the hook beneath the wire; and
   pulling the hook up relative to the wire to test the bond strength.

* * * * *